(12) United States Patent
Kikugawa et al.

(10) Patent No.: US 8,673,815 B2
(45) Date of Patent: Mar. 18, 2014

(54) HERBICIDAL COMPOSITION

(75) Inventors: Hiroshi Kikugawa, Osaka (JP); Ryu Yamada, Kusatsu (JP); Hiroyuki Okamoto, Kusatsu (JP); Takashi Terada, Kusatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 13/988,394

(22) PCT Filed: Nov. 24, 2011

(86) PCT No.: PCT/JP2011/077736
§ 371 (c)(1),
(2), (4) Date: Jun. 12, 2013

(87) PCT Pub. No.: WO2012/070688
PCT Pub. Date: May 31, 2012

(65) Prior Publication Data
US 2013/0260997 A1    Oct. 3, 2013

(30) Foreign Application Priority Data
Nov. 26, 2010    (JP) .................................. 2010-263748

(51) Int. Cl.
*A01N 43/60*    (2006.01)
(52) U.S. Cl.
USPC ...................................................... 504/136
(58) Field of Classification Search
None
See application file for complete search history.

(56) References Cited

U.S. PATENT DOCUMENTS

| 5,830,827 A | 11/1998 | Maeda |
| 2006/0154824 A1 | 7/2006 | Yoshii et al. |
| 2013/0085065 A1 | 4/2013 | Kikugawa et al. |

FOREIGN PATENT DOCUMENTS

| DE | 199 28 453 A1 | 12/2000 |
| EP | 1 825 753 A2 | 8/2007 |
| JP | 9-143015 A | 6/1997 |
| JP | 2005-60369 A | 3/2005 |

OTHER PUBLICATIONS

Hiroyoshi Matsuoka et al., "Method to control perennial grass family weeds in grass involves use of 1-(4, 6-dimethoxy pyrimidine-2yl)-3-(3-trifluuoro methyl-2-pyridyl sulphonyl) urea or its salt, and N-methoxycarbonyl sulfanilamide sodium", Thomson Scientific, vol. 2001, No. 30, Weed XP0002667706, Feb. 13, 2001, pp. 1-2.
Douglas Montgomery M.S. et al., "Evaluation of Nicosulfuron, Flazasulfuron and MSMA for Johnsongrass Control in Bermudagrass Roadsides", Oklahoma Department of Transportation-Annual Report for FY 2009, Jan. 13, 2010, pp. 1-8 (according to ISR, downloaded from www.odot.org).
Search report from International Patent Appl. No. PCT/JP2011/077736, mail date is Sep. 2, 2012.
Search report from International Preliminary Report on Patentability Appl. No. PCT/JP2011/077736, mail date is Jun. 6, 2013.

*Primary Examiner* — Alton Pryor
(74) *Attorney, Agent, or Firm* — Greenblum & Bernstein, P.L.C.

(57) ABSTRACT

At present, various herbicidal compositions have been developed and used, but they are not necessarily sufficient to control undesired plants such as weeds to be controlled, and a highly active herbicidal composition has been desired.
A herbicidal composition comprising 1-(4,6-dimethoxypyrimidin-2-yl)-3-(3-trifluoromethyl-2-pyridylsulfonyl) urea or its salt and 2-(4,6-dimethoxypyrimidin-2-ylcarbamoylsulfamoyl)-N,N-dimethylnicotinamide or its salt, and a method for controlling undesired plants using it.

16 Claims, No Drawings

HERBICIDAL COMPOSITION

TECHNICAL FIELD

The present invention relates to a herbicidal composition comprising (A) flazasulfuron or its salt (hereinafter referred to as compound (A)) and (B) nicosulfuron or its salt (hereinafter referred to as compound (B)).

BACKGROUND ART

Patent Document 1 discloses a granular herbicidal composition comprising flazasulfuron or its salt, a stabilizer and a carrier. Further, Patent Document 2 discloses a herbicidal composition comprising a sulfonylurea compound or its salt and an alkoxylated glyceride. However, Patent Documents 1 and 2 failed to specifically disclose a specific combination of compound A and compound B and synergistic effects obtainable when they are combined.

PRIOR ART DOCUMENTS

Patent Documents

Patent Document 1: JP-A-9-143015
Patent Document 2: JP-A-2005-60369

DISCLOSURE OF INVENTION

Technical Problem

At present, various herbicidal compositions have been developed and used, but they are not necessarily sufficient to control undesired plants such as weeds to be controlled, and a highly active herbicidal composition has been desired.

Solution to Problem

By combining compound A and compound B, a highly active herbicidal composition can be provided.

Advantageous Effects of Invention

According to the present invention, a highly active herbicidal composition can be provided.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E = \alpha + \beta - (\alpha \times \beta \div 100)$$

where $\alpha$: growth inhibition rate when treated with x (g/ha) of herbicide X, $\beta$: growth inhibition rate when treated with y (g/ha) of herbicide Y, E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

In compound A, flazasulfuron (common name) is 1-(4,6-dimethoxypyrimidin-2-yl)-3-(3-trifluoromethyl-2-pyridylsulfonyl)urea.

In compound B, nicosulfuron (common name) is 2-(4,6-dimethoxypyrimidin-2-ylcarbamoylsulfamoyl)-N,N-dimethylnicotinamide.

The salt included in compound A and compound B may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of compound A to compound B cannot generally be defined, as it varies depending upon various conditions such as the type of the formulation, the weather conditions, and the type and the growth stage of the undesired plants, and is, for example, from 40:1 to 1:40, preferably from 20:1 to 1:15 by the weight ratio.

The herbicidally effective amounts of compounds A and B cannot generally be defined, as they vary depending upon various conditions such as the mixing ratio of compound A to compound B, the type of the formulation, the weather conditions, and the type and the growth stage of the undesired plants. However, for example, compound A is applied in an amount of from 5 to 200 g/ha, preferably from 10 to 200 g/ha, and compound B is applied in an amount of from 5 to 200 g/ha, preferably from 10 to 150 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a broad range of undesired plants such as annual weeds and perennial weeds. The weeds to be controlled by the herbicidal composition of the present invention may, for example, be cyperaceae such as green kyllinga (*Cyperus brevifolia* var. *leiolepis*), purple nutsedge (*Cyperus rotundus* L.), and amur cyperus (*Cyperus microiria* Steud.); gramineae such as quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), wild oat (*Avena fatua* L.), water foxtail (*Alopecurus aequalis* Sobol. var. amurensis (Komar.) Ohwi), American sloughgrass (*Beckmannia syzigachne* (Steud.) Fernald), downy brome (*Bromus tectorum* L.), Italian ryegrass (*Lolium multiflorum* Lam.), guineagrass (*Panicum maximum* Jacq.), reed canarygrass (*Phalaris arundinacea* L.), common reed (*Phragmites australis* (Cay.) Trin. ex Steud.), barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr.,

*Digitaria microbachne* Henr., *Digitaria horizontalis* Willd.), green foxtail (*Setaria viridis* L.), goosegrass (*Eleusine indica* L.), johnsongrass (*Sorghum halepense* L.), bermuda grass (*Cynodon dactylon* (L.) Pers.), cogongrass (*Imperata cylindrica* (L.) Beauv.), japanese paspalum (*Paspalum thunbergii* Kunth), dallisgrass (*Paspalum dilatatum* Poir.), annual bluegrass (*Poa annua* L.), panic grasses (*Panicum* spp.), marmeladegrass or signalgrass (*Brachiaria* spp.), and itchgrass (*Rottboellia cochinchinensis* (LOUR.) W. D. CLAYTON); scrophulariaceae such as persian speedwell (*Veronica persica* Poir.), and corn speedwell (*Veronica arvensis* L.); compositae such as beggarticks (*Bidens* spp.), hairy fleabane (*Conyza bonariensis* (L.) Cronq.), horseweed (*Erigeron canadensis* L.), dandelion (*Taraxacum officinale* Weber), and common cocklebur (*Xanthium strumarium* L.); leguminosae such as white clover (*Trifolium repens* L.); caryophyllaceae such as sticky chickweed (*Cerastium glomeratum* Thuill.), and common chickweed (*Stellaria media* L.); euphorbiaceae such as garden spurge (*Euphorbia hirta* L.), and threeseeded copperleaf (*Acalypha australis* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.), and henbit (*Lamium amplexicaule* L.); malvaceae such as velvetleaf (*Abutilon theophrasti* MEDIC.), and prickly sida (*Sida spinosa* L.); convolvulaceae such as tall morningglory (*Ipomoea purpurea* L.), and field bindweed (*Convolvulus arvensis* L.); chenopodiaceae such as common lambsquarters (*Chenopodium album* L.); portulacaceae such as common purslane (*Portulaca oleracea* L.); amaranthaceae such as redroot pigweed (*Amaranthus retroflexus* L.); solanaceae such as black nightshade (*Solanum nigrum* L.); polygonaceeae such as spotted knotweed (*Polygonum lapathifolium* L.), and green smartweed (*Polygonum scabrum* MOENCH); cruciferae such as flexuous bittercress (*Cardamine flexuosa* WITH.); cucurbitaceae such as burcucumber (*Sicyos angulatus* L.); and commelinaceae such as common dayflower (*Commelina communis* L.).

The herbicidal composition of the present invention is very useful in practical application. For example, the herbicidal composition of the present invention has remarkable synergistic effects, and has favorable herbicidal effects even if the doses of both compounds A and B are small, and accordingly, the impact on the surrounding environment can be suppressed. Further, the herbicidal composition of the present invention can control perennial grass weeds such as quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), johnsongrass (*Sorghum halepense* L.), bermuda grass (*Cynodon dactylon* (L.) Pers.), dallisgrass (*Paspalum dilatatum* Poir.), cogongrass (*Imperata cylindrica* (L.) Beauv.), japanese paspalum (*Paspalum thunbergii* Kunth) which are problematic as strong weeds in agricultural fields such as orchards and non-cropland such as golf courses, railway sides and roadsides. Further, the herbicidal composition of the present invention has a high herbicidal activity also against weeds in late leaf stage, such as weeds in 5-leaf stage to heading stage, and such is particularly remarkable for grass weeds. The herbicidal composition of the present invention has favorable herbicidal effects against grass weeds and broad leaf weeds either by foliar application or soil application.

The herbicidal composition of the present invention may contain other herbicidally effective component in addition to the above active ingredients, without departing from the intention and the scope of the present invention, whereby the range of weeds to be controlled, the time of application of the composition, the herbicidal activities, etc. may be improved to preferred directions. Other herbicidally effective component includes, for example, the following compounds (by common names including ones under application for approval by ISO, or test codes; common names under application for approval by ISO mean common names before approval by ISO (International Organization for Standardization)). Even when not specifically mentioned here, in a case where such compounds have salts, alkyl esters, hydrates, different crystal forms, various structural isomers, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachior-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone or ethyl[3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523).

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), bicyclopyrone, isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenopsodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, rimsulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, or a compound disclosed in the claim of WO2005092104; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin (MRC-01), etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

The herbicidal composition of the present invention may be prepared by mixing compound A and compound B, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A and compound B may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives may be from 0.001:99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.

1. Compound A and compound B are formulated together, and the formulation is applied as it is.

2. Compound A and compound B are formulated together, the formulation is diluted to a predetermined concentration with e.g. water, and as the case requires, a spreader (such as a surfactant, a vegetable oil or a mineral oil) is added for application.

3. Compound A and compound B are separately formulated and applied as they are.

4. Compound A and compound B are separately formulated, and they are diluted to a predetermined concentration with e.g. water, and as the case requires, a spreader (such as a surfactant, a vegetable oil or a mineral oil) is added for application.

5. Compound A and compound B are separately formulated, and the formulations are mixed when diluted to a predetermined concentration with e.g. water, and as the case requires, a spreader (such as a surfactant, a vegetable oil or a mineral oil) is added for application.

Preferred embodiments of the present invention will be described below, but the present invention is by no means restricted thereto.

(1) A herbicidal composition comprising (A) flazasulfuron or its salt and (B) nicosulfuron or its salt in a mixing ratio of from 40:1 to 1:40 by the weight ratio.

(2) A method for controlling undesired plants or inhibiting their growth, which comprises applying a herbicidal composition comprising (A) flazasulfuron or its salt in a ratio of from 5 to 200 g/ha and (B) nicosulfuron or its salt in a ratio of from 5 to 200 g/ha, to the undesired plants or to a place where they grow.

(3) A method for controlling undesired plants or inhibiting their growth, which comprises applying (A) flazasulfuron or its salt in an amount of from 5 to 200 g/ha and (B) nicosulfuron or its salt in an amount of from 5 to 200 g/ha to the undesired plants or to a place where they grow.

(4) The method according to the above (2) or (3), wherein the undesired plants are weeds in 5-leaf stage to heading stage.

(5) The method according to the above (4), wherein the weeds are grass weeds.

(6) The method according to the above (5), wherein the grass weeds are at least one member selected from the group consisting of quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), wild oat (*Avena fatua* L.), water foxtail (*Alopecurus aequalis* Sobol. var. amurensis (Komar.) Ohwi), American sloughgrass (*Beckmannia syzigachne* (Steud.) Fernald), downy brome (*Bromus tectorum* L.), Italian ryegrass (*Lolium multiflorum* Lam.), guineagrass (*Panicum maximum* Jacq.), reed canarygrass (*Phalaris arundinacea* L.), common reed (*Phragmites australis* (Cay.) Trin. ex Steud.), barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L), goosegrass (*Eleusine indica* L.), johnsongrass (*Sorghum halepense* L.), bermuda grass (*Cynodon dactylon* (L) Pers.), cogongrass (*Imperata cylindrica* (L) Beauv.), japanese paspalum (*Paspalum thunbergii* Kunth), dallisgrass (*Paspalum dilatatum* Poir.), annual bluegrass (*Poa annua* L.), panic grasses (*Panicum* spp.), marmeladegrass or signalgrass (*Brachiaria* spp.), and itchgrass (*Rottboellia cochinchinensis* (LOUR.) W. D. CLAYTON).

(7) The method according to the above (2) or (3), wherein the undesired plants are perennial grass weeds.

(8) The method according to the above (7), wherein the perennial grass weeds are at least one member selected from the group consisting of quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), johnsongrass (*Sorghum halepense* L.), bermuda grass (*Cynodon dactylon* (L.) Pers.), dallisgrass (*Paspalum dilatatum* Poir.), cogongrass (*Imperata cylindrica* (L.) Beauv.) and japanese paspalum (*Paspalum thunbergii* Kunth).

EXAMPLES

Now, the present invention will be described in further detail with reference to Examples. However, the present invention is by no means restricted to such specific Examples.

Test Example 1

Upland field soil was put into a 1/1,000,000 ha pot, and seeds of crabgrass (*Digitaria sanguinalis*.) were sown. When the crabgrass reached 3.8 to 4.0-leaf stage, predetermined amounts of water dispersible granules comprising flazasulfuron as an active ingredient (trade name: SHIBAGEN DF manufactured by Ishihara Sangyo Kaisha, Ltd.) and an emulsifiable concentrate comprising nicosulfuron as an active ingredient (trade name: ONEHOPE NYUZAI manufactured by Ishihara Sangyo Kaisha, Ltd.) were diluted with water (corresponding to 300 L/ha) containing 0.1 vol % of an agricultural adjuvant (trade name: KUSARINOH manufactured by NIHON NOHYAKU CO., LTD.) and applied for foliar treatment by a small sprayer.

On the 28th day after treatment, the state of growth of the crabgrass was visually observed to determine the growth inhibition rate in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| Compound | Dose (g/ha) | Growth inhibition rate (%) of crabgrass | |
|---|---|---|---|
| | | Measured value | Calculated value |
| Flazasulfuron | 12.5 | 87 | — |
| Nicosulfuron | 15 | 7 | — |
| | 40 | 22 | — |
| Flazasulfuron + Nicosulfuron | 12.5 + 15 | 100 | 88 |
| | 12.5 + 40 | 100 | 90 |

Test Example 2

Upland field soil was put into a 1/1,000,000 ha pot, and seeds of bermuda grass (*Cynodon dactylon* (L.) Pers.) were sown. When the bermuda grass reached 5.0 to 7.0-leaf stage, predetermined amounts of water dispersible granules comprising flazasulfuron as an active ingredient (trade name: SHIBAGEN DF) and an emulsifiable concentrate comprising nicosulfuron as an active ingredient (trade name: ONEHOPE NYUZAI) were diluted with water (corresponding to 1,000 L/ha) containing 0.05 vol % of an agricultural adjuvant (trade name: KUSARINOH) and applied for foliar treatment by a small sprayer.

On the 21st day after treatment, the state of growth of the bermuda grass was visually observed to determine the growth inhibition rate. The growth inhibition rate (%) (measured value) and the growth inhibition rate (%) calculated in the same manner as in Test Example 1 are shown in Table 2.

TABLE 2

| Compound | Dose (g/ha) | Growth inhibition rate (%) of bermuda grass | |
|---|---|---|---|
| | | Measured value | Calculated value |
| Flazasulfuron | 10 | 0 | — |
| | 200 | 45 | — |
| Nicosulfuron | 10 | 8 | — |
| | 150 | 90 | — |
| Flazasulfuron + Nicosulfuron | 200 + 10 | 73 | 49 |
| | 10 + 150 | 97 | 90 |

INDUSTRIAL APPLICABILITY

According to the present invention, a herbicidal composition having a wide herbicidal spectrum, having high activity and having a long lasting effect can be provided. Further, according to the present invention, widening of the herbicidal spectrum particularly against grass weeds and application to genetically-modified crops resistant to ALS inhibitors are possible, and an increase in the application site can be expected.

The entire disclosure of Japanese Patent Application No. 2010-263748 filed on Nov. 26, 2010 including specification, claims and summary is incorporated herein by reference in its entirety.

The invention claimed is:

1. A synergistic herbicidal composition comprising (A) flazasulfuron or its salt and (B) nicosulfuron or its salt.

2. The composition according to claim 1, wherein the mixing ratio of (A) to (B) is from 40:1 to 1:40 by the weight ratio.

3. A method for controlling undesired plants or inhibiting their growth, which comprises applying a herbicidally effective amount of a synergistic herbicidal composition comprising (A) flazasulfuron or its salt and (B) nicosulfuron or its salt, to the undesired plants or to a place where the plants grow.

4. A method for controlling undesired plants or inhibiting their growth, which comprises applying a synergistic combination of a herbicidally effective amount of (A) flazasulfuron or its salt and a herbicidally effective amount of (B) nicosulfuron or its salt, to the undesired plants or to a place where the plants grow.

5. The method according to claim 3, wherein (A) is applied in an amount of from 5 to 200 g/ha, and (B) is applied in an amount of from 5 to 200 g/ha.

6. The method according to claim 3, wherein the undesired plants are weeds in 5-leaf stage to heading stage.

7. The method according to claim 6, wherein the weeds are grass weeds.

8. The method according to claim 7, wherein the grass weeds are at least one member selected from the group consisting of quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), wild oat (*Avena fatua* L.), water foxtail (*Alopecurus aequalis* Sobol. var. amurensis (Komar.) Ohwi), American sloughgrass (*Beckmannia syzigachne* (Steud.) Fernald), downy brome (*Bromus tectorum* L.), Italian ryegrass (*Lolium multiflorum* Lam.), guineagrass (*Panicum maximum* Jacq.), reed canarygrass (*Phalaris arundinacea* L.), common reed (*Phragmites australis* (Cay.) Trin. ex Steud.), barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Wilid.), green foxtail (*Setaria viridis* L.), goosegrass (*Eleusine indica* L.), johnsongrass (*Sorghum halepense* L.), bermuda grass (*Cynodon dactylon* (L.) Pers.), cogongrass (*Imperata cylindrica* (L.) Beauv.), japanese paspalum (*Paspalum thunbergii* Kunth), dallisgrass (*Paspalum dilatatum* Poir.), annual bluegrass (*Poa annua* L.), panic grasses (*Panicum* spp.), marmeladegrass or signalgrass (*Brachiaria* spp.), and itchgrass (*Rottboellia cochinchinensis* (LOUR.) W. D. CLAYTON).

9. The method according to claim 3, wherein the undesired plants are perennial grass weeds.

10. The method according to claim 9, wherein the perennial grass weeds are at least one member selected from the group consisting of quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), johnsongrass (*Sorghum halepense* L.), bermuda grass (*Cynodon dactylon* (L.) Pers.), dallisgrass (*Paspalum dilatatum* Poir.), cogongrass (*Imperata cylindrica* (L.) Beauv.) and japanese paspalum (*Paspalum thunbergii* Kunth).

11. The method according to claim 4, wherein (A) is applied in an amount of from 5 to 200 g/ha, and (B) is applied in an amount of from 5 to 200 g/ha.

12. The method according to claim 4, wherein the undesired plants are weeds in 5-leaf stage to heading stage.

13. The method according to claim 12, wherein the weeds are grass weeds.

14. The method according to claim 13, wherein the grass weeds are at least one member selected from the group consisting of quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylic glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), wild oat (*Avena fatua* L.), water foxtail (*Alopecurus aequalis* Sobol. var. amurensis (Komar.) Ohwi), American sloughgrass (*Beckmannia syzigachne* (Steud.) Fernald), downy brome (*Bromus tectorum* L.), Italian ryegrass (*Lolium multiflorum* Lam.), guineagrass (*Panicum maximum* Jacq.), reed canarygrass (*Phalaris arundinacea* L.), common reed (*Phragmites australis* (Cay.) Trin. ex Steud.), barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), goosegrass (*Eleusine indica* L.), johnsongrass (*Sorghum halepense* L.), bermuda grass (*Cynodon dactylon* (L.) Pers.), cogongrass (*Imperata cylindrica* (L.) Beauv.), japanese paspalum (*Paspalum thunbergii* Kunth), dallisgrass (*Paspalum dilatatum* Poir.), annual bluegrass (*Poa annua* L.), panic grasses (*Panicum* spp.), marmeladegrass or signalgrass (*Brachiaria* spp.), and itchgrass (*Rottboellia cochinchinensis* (LOUR.) W. D. CLAYTON).

15. The method according to claim 4, wherein the undesired plants are perennial grass weeds.

16. The method according to claim 15, wherein the perennial grass weeds are at least one member selected from the group consisting of quackgrass (*Agropyron repens* (L.) P. Beauv.), Cholorado bluestem (*Agropyron tsukushiense* (Honda) Ohwi var. transiens (Hack.) Ohwi), redtop (*Agrostis alba* L.), orchardgrass (*Dactylis glomerata* L.), perennial ryegrass (*Lolium perenne* L.), eulaliagrass (*Miscanthus sinensis* Anderss.), knotgrass (*Paspalum distichum* L.), bahiagrass (*Paspalum notatum* Flugge), johnsongrass (*Sorghum halepense* L.), bermuda grass (*Cynodon dactylon* (L.) Pers.), dallisgrass (*Paspalum dilatatum* Poir.), cogongrass (*Imperata cylindrica* (L.) Beauv.) and japanese paspalum (*Paspalum thunbergii* Kunth).

* * * * *